United States Patent
Quadling et al.

(10) Patent No.: US 8,144,336 B2
(45) Date of Patent: *Mar. 27, 2012

(54) OPTICAL COHERENCE TOMOGRAPHY IMAGING

(75) Inventors: Mark Quadling, Plano, TX (US);
Henley Quadling, Addison, TX (US);
Alan Blair, St. Paul, MN (US)

(73) Assignee: D4D Technologies, LLC, Richardson, TX (US)

( * ) Notice: Subject to any disclaimer, the term of this patent is extended or adjusted under 35 U.S.C. 154(b) by 847 days.

This patent is subject to a terminal disclaimer.

(21) Appl. No.: 12/098,928

(22) Filed: Apr. 7, 2008

(65) Prior Publication Data

US 2011/0058179 A1 Mar. 10, 2011

Related U.S. Application Data

(63) Continuation of application No. 10/840,480, filed on May 5, 2004, now Pat. No. 7,355,721.

(60) Provisional application No. 60/468,759, filed on May 8, 2003.

(51) Int. Cl.
*G01B 11/02* (2006.01)
*G01B 9/02* (2006.01)

(52) U.S. Cl. .................. 356/511; 356/479; 356/497

(58) Field of Classification Search .......... 356/451, 356/477, 479, 511; 250/227.19, 227.27; 385/12

See application file for complete search history.

(56) References Cited

U.S. PATENT DOCUMENTS

| 6,179,611 B1 | 1/2001 | Everett et al. |
| 6,377,349 B1 | 4/2002 | Fercher |
| 7,355,721 B2 * | 4/2008 | Quadling et al. ............. 356/511 |

FOREIGN PATENT DOCUMENTS

WO    WO 9957507    11/1999

OTHER PUBLICATIONS

L.L. Otis, M.J. Everett, U.S. Sathyam, B.W. Colston, "Optical Coherence Tomography: A New Imaging Technology for Dentistry," The Journal of the American Dental Association (JADA), vol. 131, no. 4, Apr. 2000, pp. 511-514.

Supplementary European Search Report, The Hague, completed May 15, 2009, 3 pages.

* cited by examiner

*Primary Examiner* — Michael A Lyons
(74) *Attorney, Agent, or Firm* — Haynes and Boone, LLP

(57) ABSTRACT

A digitized image of an object may include representations of portions of the object that are obscured, occluded or otherwise unobservable. The image may be a multi-dimensional visual representation of dentition. Characteristics of the dentition and its surfaces, contours, and shape may be determined and/or analyzed. A light may be directed toward and reflected from the dentition. The reflected light may be combined with a reference to determine characteristics of the dentition, including obscured areas such as subgingival tissue.

11 Claims, 8 Drawing Sheets

OPTICAL COHERENCE TOMOGRAPHY IMAGING

PRIORITY AND CROSS-REFERENCE TO RELATED APPLICATIONS

This application is based on and claims priority to Ser. No. 10/840,480, filed May 5, 2004, now U.S. Pat. No. 7,355,721, which application claimed priority to Ser. No. 60/468,759, filed on May 5, 2003.

BACKGROUND OF THE INVENTION

1. Related Field

The invention relates to the imaging of tangible objects, and in particular to multi-dimensional imaging of tangible objects.

2. Description of the Related Art

Some imaging technology use a triangulation technique to image an object. Imaging technologies may be used in dentistry for both intra-oral and extra-oral applications. While triangulation may be reliable and effective to image dental models, in some circumstances, reflections from translucent dentition may lessen the perception of an object.

Intra-oral imaging systems may also be susceptible to operator movement. A movement may affect the system's ability to capture an accurate depiction of an object. Intra-oral imaging systems also may have limited ability to capture dentition above the gum line. Intra-oral imaging systems may not capture images of internal, underlying, or occluded structures such as portions of dentition that are in close proximity to contiguous or nearby dentition or obscured by gingival and/or tartar.

BRIEF SUMMARY OF THE INVENTION

An Optical Coherence Tomography (OCT) imaging embodiment may digitize or capture visual images of tangible objects. The embodiments may digitize the tangible objects, or portions thereof, including areas of the objects that may be obscured and/or occluded.

An OCT imaging embodiment may generate one-, two-, three-, or other multi-dimensional images, or visual representations, of an object. The images may outline multi-dimensional surfaces, structures, contours, and other forms sizes, distances, and/or colors of the object that are obstructed. The object may include intra-oral dentition and extra-oral dental models.

An OCT imaging embodiment may include a broadband light source, a reference arm, a projector, a coupler, a sensor, and a processor. The broadband light source may generate a structured light that is projected toward an object. The structured light may be provided to the reference arm, which generates a reference beam using the structured light. Light reflected from the object and the reference beam may be combined at the coupler to create a superimposed interference pattern. The interference pattern may be detected by a sensor which that generates signals representative of superimposed interference pattern. Using an input signal, the processor may generate a dataset representative of the characteristics of the object. The dataset may be used to generate a multi-dimensional image of the object and may include image enhancement and data compression. The dataset may be used to form a model of the object. The processor may also analyze, manipulate, store or further process the dataset based on time domain analysis, Fourier Domain analysis (also known as Spectral Domain analysis) or a combination of time domain and Fourier domain analysis.

Other systems, methods, features and advantages of the invention will be, or will become, apparent to one with skill in the art upon examination of the following figures and detailed description. It is intended that all such additional systems, methods, features and advantages be included within this description, be within the scope of the invention, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION

An optical Coherence Tomography ("OCT") embodiment may capture images of an object. The images may include portions of the object that are not visible, obscured, occluded or otherwise not observable by a line of sight. The object may be an intra-oral tissue or one or more dental items, such as a tooth, multiple teeth, one or more preparations, one or more restorations or a dental arch, for example.

An OCT imaging embodiment may identify faults and voids on an interior portion of a tooth, may detect decay of interior portions of dentition, and may detect the presence and/or extent of sub-gingival tartar. The images captured by an OCT imaging embodiment may verify presence and degree of tooth damage such as cracks and assist in the preparation of dental procedures, including root canals. The images of obscured areas may reduce or eliminate invasive procedures that require removal of tissue to view or inspect the obscured areas.

Figure 1:
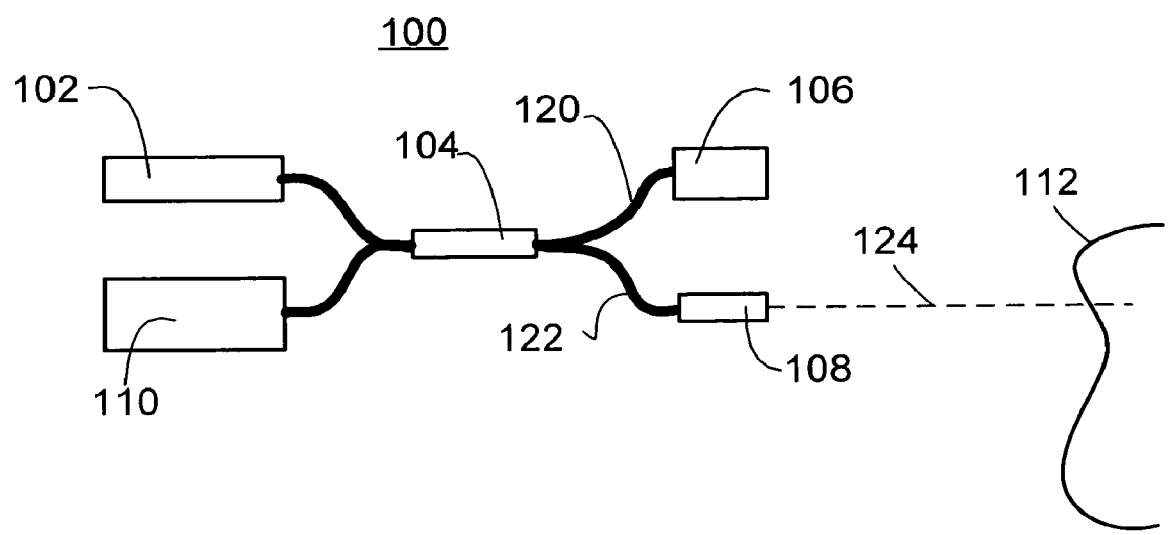
FIG. 1 illustrates an optical coherence tomography ("OCT") imaging embodiment.

FIG. 1 illustrates an exemplary OCT imaging system 100. The OCT imaging system 100 may include a light source 102, an optical coupler or beam splitter 104, a reference arm 106, a projector 108, and a sensor 110. The OCT imaging system 100 also may be coupled to a processor (not shown in FIG. 1).

The light source 102 may convert incident electromagnetic radiation of multiple frequencies to a coherent visible of invisible beam of light. The light source 102 may be a broadband device such as an LED or semiconductor pumped laser source such as a laser diode. The light may comprise constituent wavelength or one or more frequencies of coherent light. The constituent wavelengths of the light may lie in the range of about 600 to about 1700 nm. In one embodiment, the constituent wavelengths may lie the range of about 600 to about 900 nm. In an alternative embodiment, the wavelengths may lie in the range of about 1100 to about 1700 nm. In another embodiment, the wavelengths may be in the infra-red region. In yet another embodiment the wavelengths are in the range of visible light.

The light may pass through or be guided by various optical devices. The optical devices may scan, focus, polarize, expand, split, and/or direct the beam of light. The optical components may generate a structured light pattern. In an embodiment, the optical devices may generate a focused beam or dot light that may be moved or scanned along a structured pattern. The optical devices may include mirrors, lenses, relays, guides, splitters, gratings, scanners, polarizers etc. and combinations of these devices.

The optical coupler (beam splitter) 104 may be coupled to the light source 102 through an optical instrument. The optical coupler 104 may be optically coupled to the light source 102 through an optic cable, an optical guide wire, an optical relay, free-space optics, and any other light transmitting technology, or any combination thereof. The optical coupler 104 may also be a unitary part of the light source 102.

The optical coupler 104 may separate, divide or split the structured light into multiple paths. In an embodiment, the optical coupler 104 splits the structured light into two or more paths that include a first optical path 120 and a second optical path 122. The first optical path 120 and the second optical path 122 may include various light transmitting instruments or devices that guide the structured light to a destination. In one embodiment, the first optical path 120 and the second optical path 122 may be strands of transparent material, such special types of glass and plastics that carry optical signals. It may also include optical fibers, a bundled fiber optic cable, an optical guide wire, an optical relay, free-space optics, or any one or combination thereof. The first optical path 120 guides the light to the reference arm 106. The second optical path 122 guides the light to the projector 108.

The reference arm 106 may receive the light through the first optical path 122 and reflect the light toward the coupler 104. The light reflected from the reference arm 106 may return to the coupler 104 through the first optical path 120. A reference arm 106 may include a light path having an optical fiber optically coupled to a collimator or focusing optics and a minor. The light path directs the light to the mirror, which may reflect the light along the light path.

The reflected light through the light path may include most of the constituent components of the structured light from the light source 102. The light may be substantially unaffected or altered by reference arm 106 or the coupler 104. A baseline measurement of the traveled distance of each of the constituent components of the light may be measured. The baseline measurement may provide a reference for a measurement of traveled distance of the reflected light. The baseline measurement may be compared with the distances other light originating from the light source 102 passes through media other than air may travel, such as the distance light reflected from the object 112 may travel. The comparison may include superimposing the baseline measurement of the light returned from the reference arm 106 with any other light reflected from the object 112. Based on an interference pattern of the superimposition, a distance traveled by the reflected light may be determined. For example, a known distance between the light traveling through reference arm 106 and returned to the coupler 104 may be equal to a distance traveled by any other light returned to the coupler and combined with the reflected light. Variations may be detected to determine surface characteristics of the object 112.

The projector 108 may be coupled to the coupler through a second optical path 122. The projector 108 may be portable and/or handheld. The projector may be manipulated or inserted into an oral cavity. The projector 108 may focus or otherwise direct structured light 124 toward an object 112. The projector 108 may project the beam of light 124 toward the object 112 in a varied or structured pattern. The light 124 may converge all or a portion of the object 112. The light 124 also may be focused on structures that prevent the light from illuminating the object 112. For example, if the object 112 is a tooth and the light 124 may be so that a light pattern is projected onto the tooth. The light 124 also may be directed toward gum tissue surrounding or near a sub-gingival portion of the tooth. The pattern may be projected on the tooth, the gum tissue, or any part or combination of the oral cavity. The beam of light 124 may be direct towards the dentition so that the structured pattern is reflected therefrom.

The projector 108 may also detect the light reflected from the object 112. The reflected light may be directed along a return path to the coupler 104. The return path may be substantially parallel to the first optical path 122. The return path may also coincide with the first optical path 122 in a reverse direction.

The reflected light may strike the surface of the coupler. The coupler 104 may combine the reflected light with light returned from the reference arm 106. When the combined lights interfere with each other, the interference may create a superimposed interference light pattern. The superimposed light pattern may detect a shape, distribution and composition that represent surface characteristics of the object 112. The surface characteristics may include both exterior surfaces and interior surfaces. The surface characteristics also may include characteristics of surfaces that are obscured, occluded or otherwise hidden from a normal view.

The surface characteristics may be identified by detecting differences in color, shading, intensity and distance through reflections of portions of the light from the surface of the object 112. In one embodiment, the light reflected from the reference arm 106 and the light reflected from the object 112 may originate from light source 102. The constituent components of the light reflected from the reference arm 106 may be substantially similar to the respective components of the sourced light. The distance traveled by the light within the reference arm 106 may be known or predetermined and provide a baseline used to render an image. The baseline may include the constituent components of the source light and the distance traveled by the source light.

The reflected light may be reflected from an exterior surface of the object 112. The light may also penetrate the surface of the object 112 and be reflected from an interior surface of the object 112. For example, a portion of the light may be reflected from the exterior surface of the object and a portion of the light may be reflected from as an interface between materials within the object 112, or from an occluded surface. Constituent components of the source light may be reflected or absorbed, based on properties of the object including any constituent materials, and interfaces between materials of the object 112. The reflected light from the object 112 may include constituent parts of the original sourced light or may be substantially different from the original sourced light. In addition, the light reflected from the object may be reflected from different distances within the object. For example, a constituent set of reflections from the object may contain constituent components that may occur at an air/gum interface, and another constituent set of reflections may be created by a gum/enamel interface.

The light reflections from various portions of the object 112 may be combined or superimposed with the baseline light at the coupler 104. By combining or superimposing the baseline light with the light reflected from the object 112 or its various surfaces, an interference may be detected. The interference properties may be provide a comparison of the baseline and the light reflected from the object 112. With the distance traveled by the light by the reference arm 106 known, the distance each reflection travels from a surface may be determined.

Since the baseline measurement includes a distribution of the constituent components of the source light 102, a type of interface at each surface on and within the object 112 may be determined based on the constituent components of the source light that are absorbed or reflected at each interface. The degree to which each interface between different materials absorbs, reflects or transmits a constituent component of the source light may depend on properties of the material and the interaction of light with the material. For each position of the light beam incident upon the object, a dataset may be determined. The dataset may be generated to represent a visual representation of the object 112.

The superimposed interference light pattern may be directed by the optical coupler 104 to the sensor 110. The sensor 110 may capture and in some embodiments may digitize the superimposed interference light pattern to generate signals that represents the shape, distribution, color, shading, and/or composition of the superimposed interference light pattern or any combination thereof.

The signals from the sensor 110 may be processed by a processor or a controller. The processor may generate a dataset that represents various characteristics of the object 112 and/or its surfaces, such as its shape, height, width, contour, and exterior arrangement, and the volume etc. The processor may use time domain or frequency domain analysis such as Fourier domain data processing. The processor may also include an image enhancement application that may improve the quality of the captured image automatically through software or manually by a user program.

Figure 2:
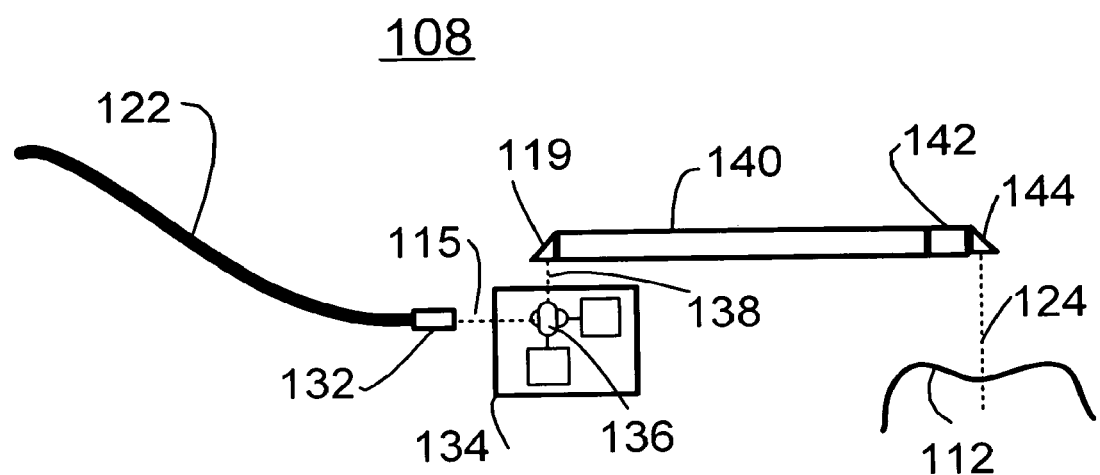
FIG. 2 illustrates a projector of an OCT imaging embodiment of FIG. 1.

FIG. 2 illustrates an exemplary projector 108. A first optical path 122 guides the light from a light source 102 to the projector 108. The projector 108 may include a focusing or collimating element 132 that directs the beam of light 115 to a scanner 134.

The scanner 134 may include one or more reflective surfaces 136. The reflective may surfaces scan the beam of light 115 along multiple axes. The scanner 420 may be a one-, two-, three-, or other multi-axis scanner. One example of a scanner 420 is described in co-owned U.S. patent application Ser. No. 10/804,694, filed on Mar. 19, 2004, now U.S. Pat. No. 7,184,150. The disclosure of the aforementioned co-owned US patent is incorporated by reference in its entirety herein. The directed beam of light 138 exits the scanner 134 and may be incident on a first prism 119 that bends or changes the direction or path of the light 138. The first prism may direct the beam of light to a relay 140. The relay 140 may be a rod or GRIN (gradient index) lens. The beam may be focused by an objective focusing element 142, and may be deflected toward the object 112 through the second prism 144. The light is incident upon the object 112. The light is projected along a path across the object 112.

The light may project a dot on the object 112 in discrete time. The dot may be scanned in a one-, two-, three, or other multi-dimensional patterns across the object 112. The incident light may be projected to a surface of the object that is obscured, occluded or otherwise not visible. The light may also be reflected from an interior surface of the object 112. Portions of the incident light may be reflected back toward the projector 108 and guided along a parallel optical path as the sourced light. Portions of the incident light may be guided in a reverse direction along the same optical path as the incident light.

Figure 3:
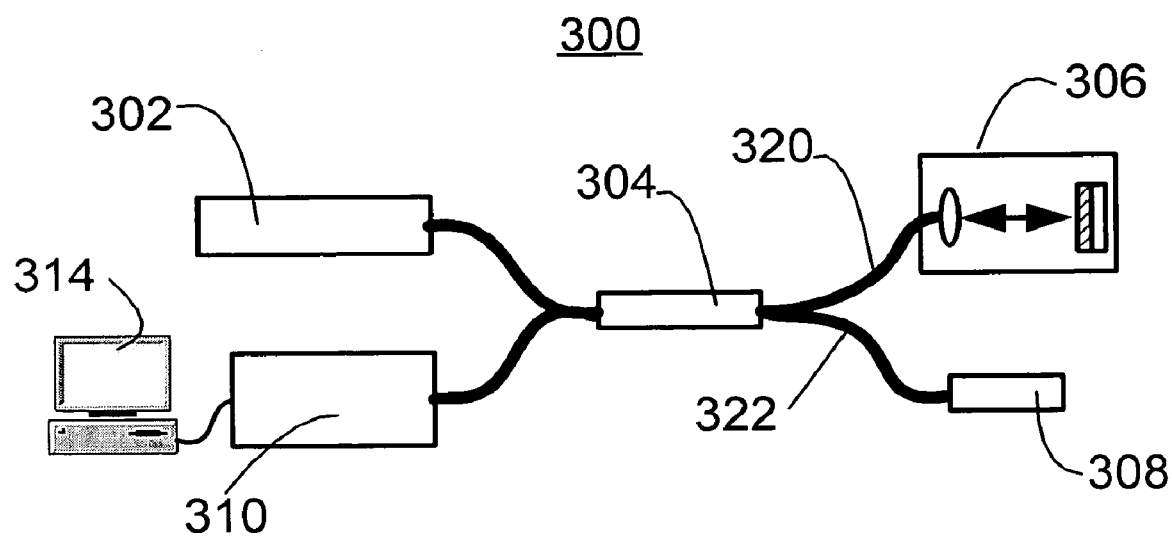
FIG. 3 illustrates a Time domain OCT imaging embodiment.

FIG. 3 illustrates an exemplary time domain OCT imaging system 300. The time domain OCT imaging system 300 may include a light source 302, a coupler 304, a projector 308, a time domain reference arm 306, and a sensor 310. The light source 302, the coupler 304 and the projector 308 may be similar to the light source 102, the coupler 104, and projector 108, respectively, described above.

The time domain reference arm 306 may be generate a time-varying path length 310 on which light from the coupler 104 may travel and be returned to the coupler 104. The time-varying path 310 creates reflected light that may be returned to the coupler 304 along a first optical path 220. The time-varying time domain reference arm 306 provides a time dependent delayed reference signal having a time delay with respect to the light transmitted from the source 102. The time-dependent delay may be based on a time of flight to the time domain reference arm 306 and along a return path. For example, the time-dependent delay may be based on a time the light travels from the coupler 304 to a reference minor and is reflected back from the reference mirror to the coupler 304. The time delayed signal may be used as a reference signal that has substantially similar characteristics to the light from transmitted from the light source 302, but being delayed in time. An example of the time-varying path length is a length of optical cable connected to a collimator or focusing optics which images the light onto a moveable minor that reflects the light back along the same optical cable.

The coupler 304 may combine the time-varying pattern with the reflected light from the object 112. When combined with the light reflected from the object 112, the combined pattern provides an interference pattern that represents the superimposition of the time-delayed reference signal. By combining the time-varying reflected light from the time-varying path length 310 with the light reflected from the object 112, the coupler may create an interference pattern that represents a depth, color or shading of the light reflected from the surface and internal structure of the object 112. The characteristics of the surface of the object 112 may be deduced based on differences in shape, color, shading, amplitude, position, features and other attributes that may be detected by the interference pattern. Similarly, a volume of the object 112 may be detected by the shape, amplitude, position and other characteristics within the interference pattern. Based on the depth of light reflected, the height of the object may be determined.

The sensor 310 that detects or measures light by converting it into an optical or electrical signal may sense the combined interference pattern from the coupler 304. The sensor 310 may generate analog or digital signals that represent the amplitude (or strength) of the interference generated from a combined reflected light from the time-varying path and the reflected light from the object 112. The sensor 310 may include a photodetector such as an array of Charge-Coupled Devices (CCD). In some embodiments, the sensor may also include a bandpass filter, an envelope detector, and analog-to-digital converter that generate discrete signals that represent the distance traveled by light reflected from the object 112.

The processor 314 may generate a dataset representing the various surfaces, contours, arrangement, shape and/or size of the object 112 based on the signals received from the sensor 310. The dataset may be used to display or print a visual representation or image of the object 112. For example, the image may be rendered on a video monitor, or other display using geometric modeling using colors and shading to give the image a realistic appearance. Similarly, the image may be transmitted to a head-mounted display that holds the image in front of the user. An example of a head-mounted display is described in co-owned application entitled Intra-Oral Imaging System, filed on Apr. 30, 2004. The description of the aforementioned application is incorporated by reference herein in its entirety. The dataset also may be used by a geometric modeling program such as a milling program or a CAM program, to render a physical model of the object 112.

Figure 4:
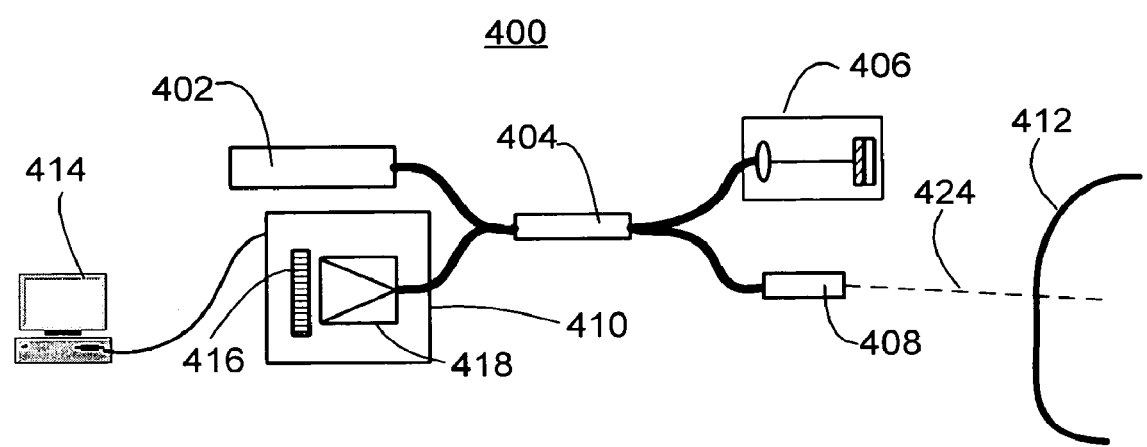
FIG. 4 illustrates a Fourier domain OCT imaging embodiment.

FIG. 4 illustrates an embodiment of a Fourier domain OCT imaging system 400 (also referred to as Spectral domain OCT imaging or Fast Fourier domain imaging). The Fourier domain OCT imaging system 400 may include a light source 402, a coupler 404, a projector 408, a fixed reference arm 406, and a sensor 410. The light source 402, the coupler 404 and the projector 408 may be similar to the light source 102, the coupler 104, and projector 108, respectively, described above.

The fixed reference arm 406 may include a fixed reflecting surface. The reflective surface may be one or more minors that reflect the light along a fixed path length. The fixed reference arm 406 may be a fixed length wave guide optically coupled to the coupler at one end and having a reflective surface at another end. The fixed reference arm 406 may also be a time-varying reference or delay as previously described.

The sensor 410 may include a spectrometer 418 that measures wavelengths or indices of refraction and a photosensor 416. The sensor 410 may receive the combined light from the coupler 404. The spectrometer 418 may include a grating that separates the combined light into various constituent components, providing a spectrograph of the combined light. The spectrograph may include various frequency components of the combined light spatially separated within a single image that constitute frequency data. Each of the constituent components may correspond to different wavelength or frequency of light that comprise the broadband light source 402. The constituent components may be in different proportions to the respective constituent components of the broadband light source 402.

The photosensor 416 may be an array of light sensitive devices, such as a CCD or CMOS or a linear array. The spectrograph from the spectrometer 418 may describe surface characteristics of the object 412. For a given point, a height of the object may be determined based on the spectrograph of a combined light. As the dot may be scanned across the surface of the object 412, height and position measurements may be measured by the photosensor. The photosensor 416 may generate signals based on the spectrograph produced by a grating.

A processor or controller 414 translates these signals to datasets that represent the characteristics of the object 112. The processor may generate a dataset according through an inverse Fourier Transform such as an inverse Fast Fourier Transform performed on the data collected from the spectrograph. Based on the inverse Fourier Transform the frequency data is translated from the frequency domain into the spatial domain. The frequency distribution of the spectrograph from the spectrometer 418 may generate a spatial distribution according to the inverse Fourier Transformation that may include artifacts. The artifacts may be spikes that correspond to a spatial position of surfaces along the axis of the light projected toward the object 412. A multi-dimensional location of the various surfaces may be determined based on the projected beam toward the object 112.

Figure 5:
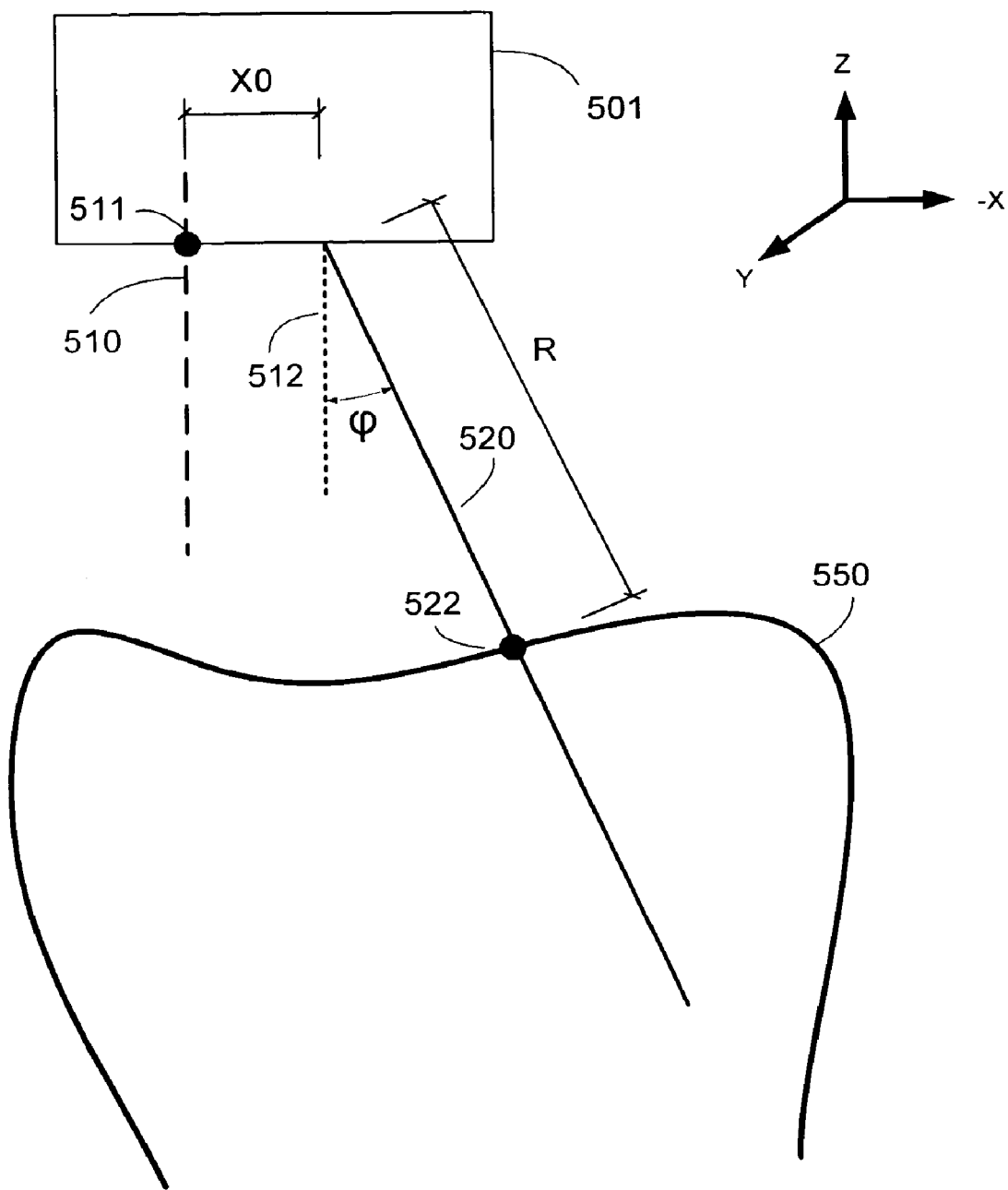
FIG. 5 illustrates a light projection of the OCT imaging embodiment of FIG. 1.

FIG. 5 illustrates a projection of a beam of light 520 in an X-Z plane. The beam 520 may be projected from the OCT imaging system 501. The beam 520 may be incident an interior or exterior area 522 of the object 550. The beam 520 also may be reflected along a common incident path 520.

From a superimposition of the reflected beam returned along the common path 520 and light from the interferometer a distance R to the surface area 522 along the beam may be determined. The surface area 522 detected may be on the first exterior surface of the object 550. In this embodiment, the beam 520 exits the OCT imaging system 501 at a distance x.sub.0 along the X-axis in the X-Z plane from the optical axis 510 of the OCT imaging system 510. The beam 520 exits the OCT imaging system 501 at an angle φ to the vertical axis 512 parallel to the Z-axis. Together, the parameters $x_0$ and φ and the projection of R in the X-Z plane characterize the location of the point 522 in the X-Z plane.

Figure 6:
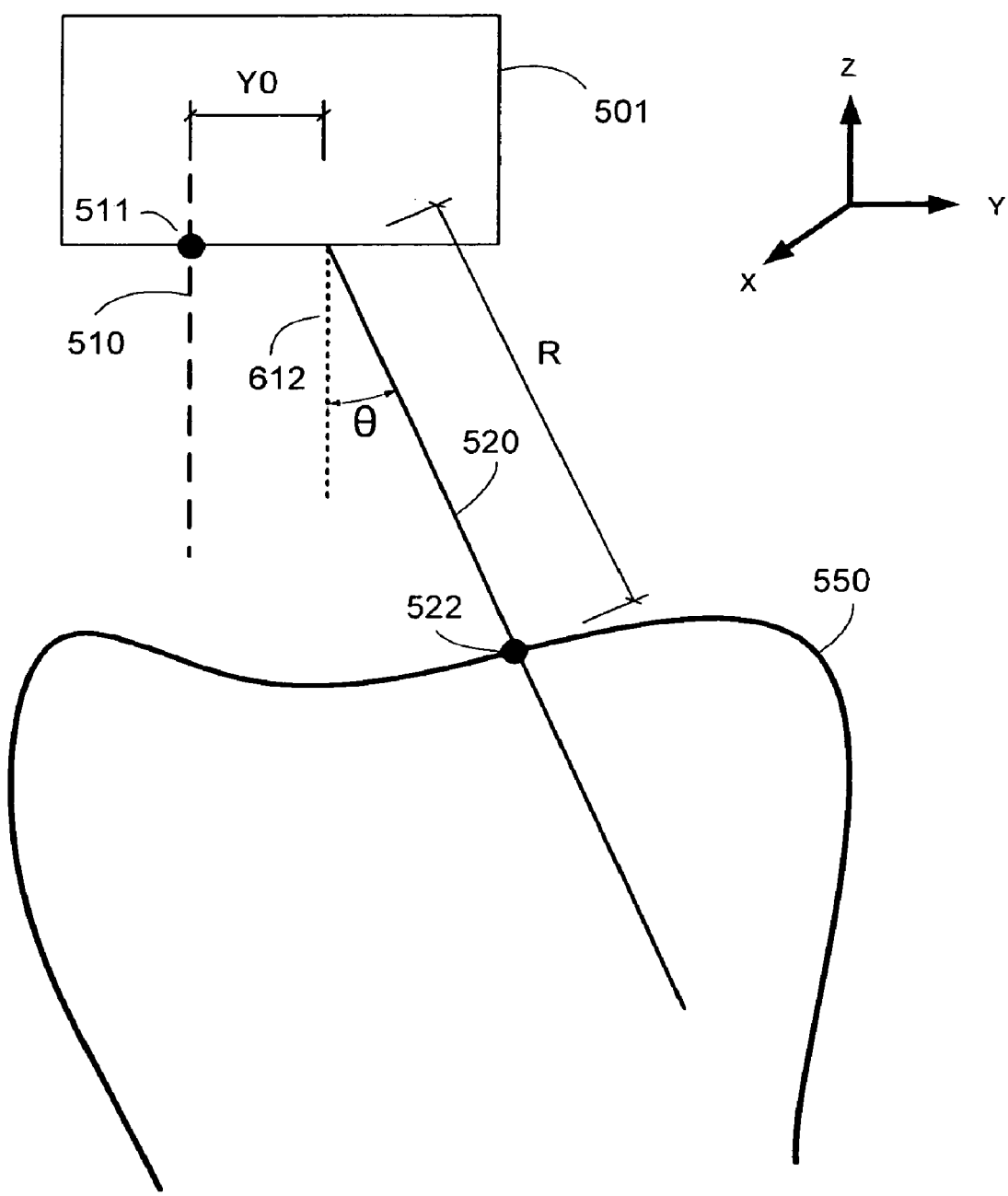
FIG. 6 illustrates a light projection the OCT imaging embodiment of FIG. 1.

FIG. 6 illustrates the configuration viewed from a perspective in the Y-Z plane. The beam 520 exits the OCT imaging system 501 at a position $y_0$ along a Y axis from an optical axis 510, at an angle θ to a vertical axis 612 parallel to the Z axis.

The parameters $x_0$, $y_0$, θ, φ and R may be used to determine a location of the position 522 relative to a point 511 on the optical axis of the OCT imaging system 501. In this embodiment, the reference point 511 is a portion of the projector. The parameters x.sub.0, y.sub.0, .theta., .phi. may be determined based on the position of the components in the projector, such as the rotational parameters of a two axis scanner. The parameters $x_0$, $y_0$, θ, φ may be determined by a calibration procedure or by some other measurement procedure. The parameters $x_0$, $y_0$, θ, φ may be uniquely determined by the orientation of the reflective surfaces in the scanner, and the fixed geometric dimensions of the OCT imaging system. The distance R may be correlated to the superimposed interference pattern of the combined. The distance R may be a measurement along the path 520, and include X, Y or Z components of the surface area 522.

The path 520 does not have to be located completely within the X-Z or Y-Z planes. Where the position of the point 522 on the surface of the object being imaged is ($x_i$, $y_i$, $z_i$), the coordinates $x_i$, $y_i$ and $z_i$ may be determined according to the parameters $x_0$, $y_0$, θ, φ and R as follows:

$$x_i = R \cos\theta \sin\phi + x0 \qquad (1)$$

$$y_i = R \cos\phi \sin\theta + y0 \qquad (2)$$

$$z_i = \{\text{square root}\}\{\text{square root over } (R^2 - ((xi-x0)^2 + (yi-y0)^2))\} \qquad (3)$$

The processor may be configured to determine the coordinates $x_i$, $y_i$, and $z_i$ based on the above parameters using these equations.

Figure 7:
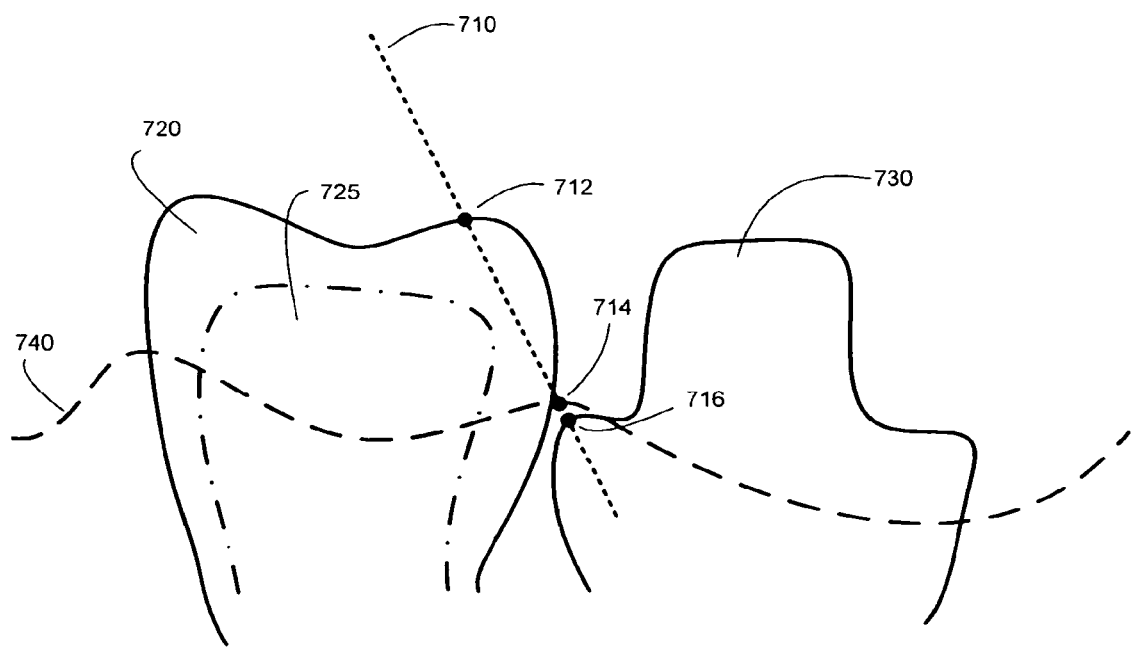
FIG. 7 illustrates an OCT embodiment digitizing a preparation.

FIG. 7 illustrates an embodiment of the OCT imaging device that may digitize a prepared tooth or preparation 730. A beam of light may converge through by an axis 710. The beam may be projected along the axis 710 to strike a surface of a preparation 730 and a neighboring tooth 720. The beam may be incident upon a surface of the neighboring tooth at a neighboring area 712 along an axis of the beam 710. Portions of the light incident at the neighboring surface area 712 may reflect back to the OCT imaging device along the same axis 710. Remaining portions of the light may pass beyond or penetrate the neighboring tooth 720, exit the neighboring tooth 720 and enter gingival tissue 740. Portions of the light may reflect back from the both the interface between the neighboring surface area 712 and the gingival tissue at 714 along the axis 710. Remaining portions of the incident light may continue along the axis 710 and may be incident upon the surface of the prepared tooth 730. Portions of the light may be reflected from a margin area 716 of the preparation 730.

The reflected light detected along the axis 710 may be analyzed to determine a position of the various surfaces areas 712, 714 and 716. A three dimensional representation, map or image of the surface of the prepared tooth 730 may be generated from a collection of determined surface areas. An image of the margin area 716 may be determined even if a direct view from the OCT imaging device may be occluded by neighboring dentition, other tissue or material.

Additional internal structures within the tooth such as dentin component 725 may also be detected. Tartar or decay present may also be detected. Various surfaces may have a unique signature in the analysis of the combined interference pattern and therefore the various surfaces may be imaged.

The surface area 712 may be an air/enamel interface with a unique distribution of reflected light. An interface area 714 may be an enamel/gingiva interface with a unique distribution of reflected light. An interface area 716 may be a gingiva/enamel interface with a unique distribution of reflected light. If a signal is detected that has the correct form and shape and strength of typical signal of light reflected from an air-enamel interface, the distance R may be determined based on a measurement of the reference path length of the reference arm path distance at the particular position which caused the signal.

Figure 8:
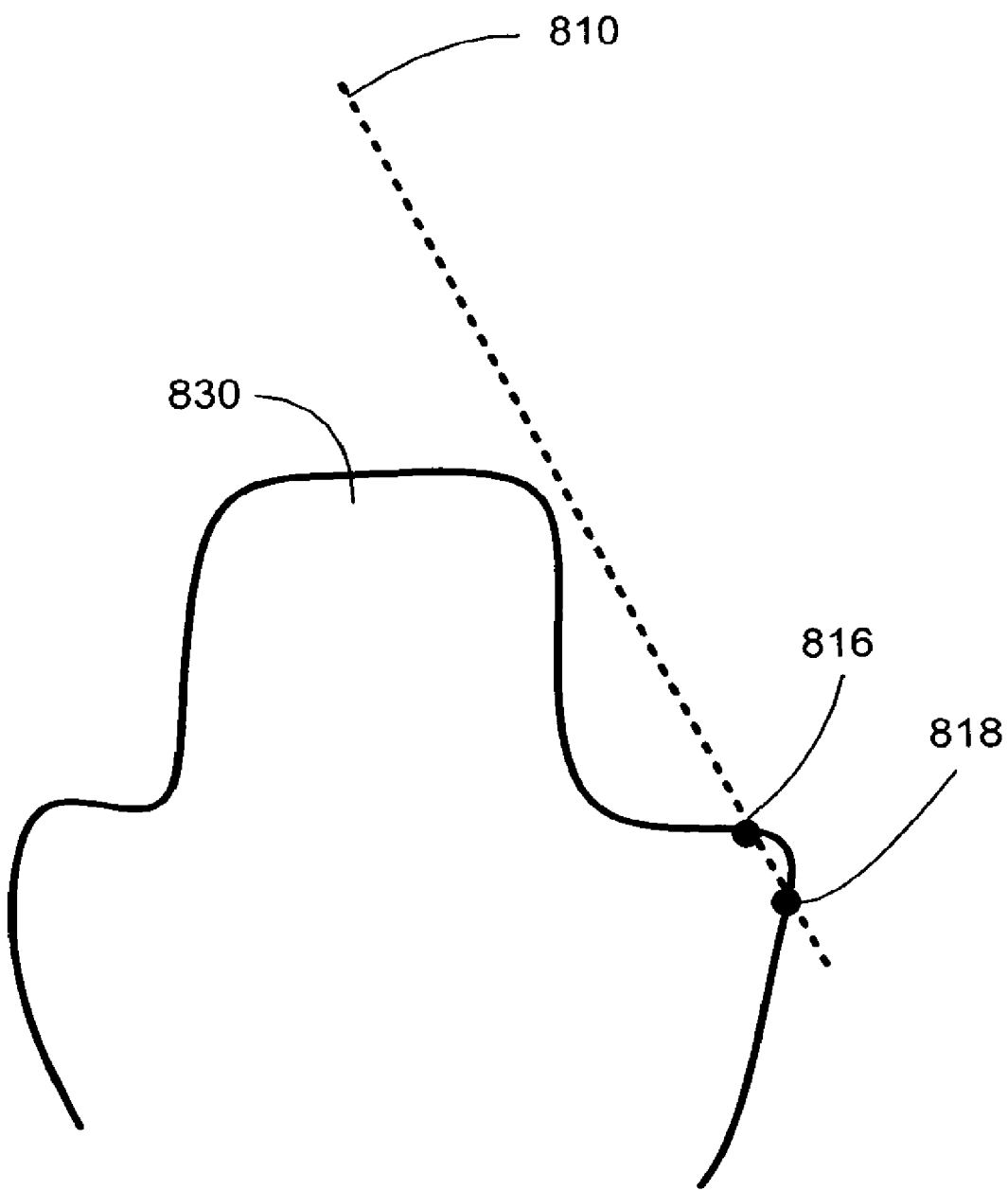
FIG. 8 illustrates an OCT embodiment for detecting a margin.

FIG. 8 illustrates an embodiment of an OCT imaging device for digitization of a shoulder or marginal ridge of a prepared tooth 830. A beam of light may be projected along the axis 810 toward the tooth 830. The beam may be incident on the prepared tooth 830 at a point above a marginal ridge 816. A portion of the light may be reflected from the surface 816 and returned along the axis 810 to the OCT imaging device. Other portions of the light may penetrate the surface area 816 and continue along the axis 810 through the prepared tooth 830. Other portions of the light may exit the prepared tooth beyond marginal ridge at the area 818. The light may also be reflected from the surface area 818. The reflected light may be analyzed to determine the location of the points above and below the marginal ridge. An intersection point of the surfaces above and below the marginal ridge may be determined, and provide an accurate margin measurement. This may be extended to the detection of various features which can be approximated as an intersection of two or more surfaces.

In another embodiment, an OCT imaging device may digitize dental molds or castings. The molds or castings may be a material that is transparent to an operating wavelength of the OCT imaging system. The surfaces of the mold not directly accessible to the OCT imaging system may be digitized by capturing images through the transparent material.

In another embodiment, an OCT imaging system non-invasively measures presence and/or amount of sub-gingival tartar. The OCT imaging system may measure a two-dimensional region through existing gingival tissue to detect tartar presence. The OCT imaging system also may measure a two-, three-, or multi-dimensional regions.

In another embodiment, a surface may be inferred by assuming smoothness of the surface locally from where surface data is available. This may occur using one-, two- or three- or other multi-dimensional interpolation techniques. For example, a bicubic or NURBS (Non Uniform Rational B-Spline Surface) patch may be fitted to a local surface, in order to infer the data that may be missing from the surface. Gaps in the surface data may be inferred via interpolation techniques as known by those experienced in the art.

A three dimensional model provided by an OCT imaging embodiment may have far ranging applications, including application in preventative dentistry, preventative diagnostic procedures, detection of gum retention, detection of tartar, and fitting and formation of restorations such as crowns bridges, onlays, inlays and other dental restorations, orthodontics, periodontal analysis, retainers and the like.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

What is claimed is:

1. A digitizer, comprising:
    a light source configured to generate a beam of structured light;
    a reference arm configured to generate a reference beam of light based on the beam of structured light;
    a projector configured to project the beam of structured light toward an object and to detect a reflection of at least a portion of the beam, the beam being projected toward the object as a dot that traverses a two dimensional (2D) pattern across a three dimensional (3D) outer surface associated with the object to generate reflection data representing the 3D outer surface associated with the object;
    a coupler configured to combine the reference beam and the reflection to generate a superimposed interference light pattern; and
    a processor configured to generate a dataset representative of the three dimensional (3D) outer surface of the object based on the superimposed interference light pattern, wherein the dataset is generated from information consisting essentially of the reflection data;
    where the object is one of: an in-vivo oral structure, and an ex-vivo dental impression.

2. The digitizer of claim 1 where the projector comprises a hand-held intraoral probe configured to be manipulated in an oral cavity.

3. The digitizer of claim 2 where the intra-oral probe projects the beam of structured light toward in vivo dentition and detects light reflected from the dentition.

4. The digitizer of claim 1 where the reference arm generates a time-varying baseline pattern and the processor is configured to generate the dataset according to time domain data processing.

5. The digitizer of claim 1 where a signal comprises a shape, distribution and composition of the superimposed interference light pattern.

6. The digitizer of claim 1 where the reference arm generates a fixed reference baseline pattern and the digitizer further comprises:
    a spectrometer configured to separate the superimposed interference light pattern to constituent components; and
    a linear photosensor configured to detect the constituent components.

7. The digitizer of claim 1 where the processor is configured to generate the dataset according to Fourier domain data processing.

8. The digitizer of claim 6 where the spectrometer comprises a grating.

9. The digitizer of claim 6 where the photosensor comprises an array of light sensitive detectors.

10. The digitizer of claim 8 where the photosensor comprises a charge coupled device.

11. The digitizer of claim 1 where the light source comprises a beam splitter configured to split the beam of structured light into a first beam and a second beam.

* * * * *

UNITED STATES PATENT AND TRADEMARK OFFICE
CERTIFICATE OF CORRECTION

PATENT NO. : 8,144,336 B2
APPLICATION NO. : 12/098928
DATED : March 27, 2012
INVENTOR(S) : Mark Quadling, Henley Quadling and Alan Blair It is certified that error appears in the above-identified patent and that said Letters Patent is hereby corrected as shown below:

Column 3, Line 44, the word "minor" should be --mirror--
Column 6, Line 24, the word "minor" should be --mirror--
Column 6, Line 31, the word "minor" should be --mirror--
Column 7, Line 23, the word "minor" should be --mirror--

Signed and Sealed this
Sixteenth Day of October, 2012

David J. Kappos
*Director of the United States Patent and Trademark Office*